United States Patent [19]
Tankovich

[11] Patent Number: 5,746,736
[45] Date of Patent: May 5, 1998

[54] CRYOGENIC LASER LITHOTRIPSY WITH ENHANCED LIGHT ABSORPTION

[75] Inventor: Nikolai Tankovich, San Diego, Calif.

[73] Assignee: Lumedics, Ltd., San Diego, Calif.

[21] Appl. No.: 512,884

[22] Filed: Aug. 9, 1995

[51] Int. Cl.$^6$ ..................................................... A61N 5/02
[52] U.S. Cl. ................................... 606/9; 606/2; 606/10; 606/21
[58] Field of Search ................... 606/2–26; 607/88–92, 607/90–105

[56] References Cited

U.S. PATENT DOCUMENTS

| | | |
|---|---|---|
| 3,660,777 | 5/1972 | Erickson . |
| 3,769,963 | 11/1973 | Goldman et al. ........................ 606/3 |
| 3,865,114 | 2/1975 | Sharon . |
| 4,211,229 | 7/1980 | Wurster . |
| 4,564,012 | 1/1986 | Shimada et al. . |
| 4,566,453 | 1/1986 | Kumano et al. . |
| 4,583,526 | 4/1986 | Ali . |
| 4,959,063 | 9/1990 | Kojima . |
| 4,976,709 | 12/1990 | Sand . |
| 5,037,421 | 8/1991 | Boutacoff et al. . |
| 5,059,192 | 10/1991 | Zaias . |
| 5,169,396 | 12/1992 | Dowlatshahi et al. . |
| 5,195,541 | 3/1993 | Obenchain . |
| 5,207,671 | 5/1993 | Franken et al. . |
| 5,217,455 | 6/1993 | Tan . |
| 5,281,213 | 1/1994 | Milder et al. ............................ 606/20 |
| 5,290,273 | 3/1994 | Tan . |
| 5,342,352 | 8/1994 | Franken et al. . |
| 5,344,418 | 9/1994 | Ghaffari . |
| 5,348,552 | 9/1994 | Nakajima et al. . |
| 5,520,680 | 5/1996 | Shapshay et al. ........................ 606/12 |

FOREIGN PATENT DOCUMENTS

| | | |
|---|---|---|
| PCT/US90/06109 | 10/1990 | WIPO . |
| PCT/US93/03612 | 4/1993 | WIPO . |

OTHER PUBLICATIONS

Inci F. Cilesiz, et al., "Light dosimetry: effects of dehydration and thermal damage on the optical properties of the human aorta" Applied Optics vol. 32(4), 1993, pp. 477–487.
Kathy Kincade, "Wrinkles shrivel under fire from pulsed lasers.", New Scientist, 1995 Jul., p. 25.
"Cosmetic lasers: in pursuit of lost youth.", Biophotonics International, 1995 Jul./Aug., pp. 61–62.

*Primary Examiner*—David M. Shay
*Attorney, Agent, or Firm*—Baker, Maxham, Jester & Meador

[57] ABSTRACT

A target region of tissue is destroyed by saturating the region with light-absorbing material, reducing the temperature of the region, and disintegrating the region with a light source. One means for carrying out these steps is a multi-channel delivery needle having a primary transport line, a waveguide lengthwise connected to the primary transport line, and one or more auxiliary lines lengthwise connected to the primary transport line. The tubes and waveguide define a sharpened common end to assist the needle in entering the skin and penetrating flesh necessary to reach the target region.

59 Claims, 2 Drawing Sheets

CRYOGENIC LASER LITHOTRIPSY WITH ENHANCED LIGHT ABSORPTION

BACKGROUND OF THE INVENTION

1. Field of the Invention

The present invention relates to the removal of undesirable tissue from a living being, such as a human. More particularly, the invention concerns a method and apparatus for destroying a target region of tissue by saturating the region with light-absorbing material, freezing the region, and disintegrating the region with laser light.

2. Description of the Related Art

Many different biological conditions require removal of unwanted tissue. When physicians detect a malignant tumor, for example, they must promptly and completely remove the tumor. Many other patients undergo surgery to remove other types of undesirable tissue, such as benign tumors, cysts, fat kidney stones, and the like.

The careful use of a scalpel is probably the most common technique for removing unwanted tissue, wherein the skin proximate the target region is incised, and the target region of tissue is severed from the body and removed. Seeking to reduce the intrusiveness of this technique, physicians and engineers have developed a number of other techniques and devices for removing unwanted tissue. For example, some have employed lasers to destroy the unwanted tissue with powerful irradiation of a laser beam. Others have used cryogenic materials to "freeze" the unwanted tissue, which is then surgically severed from the patient's body. Although these techniques may be adequate in some applications, they may not be completely satisfactory for others. Some people, for example, may complain that these extraction techniques are still too intrusive, or that they damage healthy tissue by ineffectively localizing the laser irradiation or freezing.

One approach combines laser irradiation with cryogenics in an attempt to achieve a less intrusive technique for treating tissue. In particular, this technique cryogenically reduces the skin temperature and then laser irradiates a sub-surface region through the skin to break down the sub-surface region. Cryogenically reducing the skin temperature constricts blood vessels in the skin, thereby aiding unencumbered passage of the laser beam through the skin. Although this procedure may achieve adequate results for some applications, certain users may desire a more localized procedure. In particular, this method does not establish the boundaries of the target region with sufficient precision for some applications, possibly damaging healthy neighboring tissue.

SUMMARY OF THE INVENTION

Broadly, the present invention concerns a system for destroying a well defined target region of unwanted tissue. The invention may be carried out by the process of saturating the target region with light-absorbing material, reducing the temperature of the region, and disintegrating the region with a light source. More particularly, the target region may be saturated with a stain that is particularly absorbent of a specified wavelength of light. This may be accomplished by injecting the stain through a needle to the prescribed target region. Before, after, or concurrently with the stain injection step, the target region's temperature is reduced using a low-temperature cryogenic liquid such as liquid nitrogen ("$LN_2$"). The cryogenic liquid, like the stain, may be injected through a needle to the target region. Preferably, the temperature of the target region is reduced sufficiently to solidify the target region.

After dying and freezing the target region, a source of the specified wavelength of light is imparted to the target region. The specified wavelength matches the absorption proclivity of the stain. This selective absorption results in a fragmenting of the frozen and now brittle target region. The light source preferably comprises a laser, which may be directed to the target region by an optical waveguide. After this, the fragmented target region may be removed using a device such as a vacuum source.

One means for carrying out these steps is a multi-channel delivery needle having a primary transport line, a waveguide lengthwise connected to the central primary transport line, and one or more auxiliary lines lengthwise connected to the primary transport line. The primary and auxiliary lines and the waveguide define a sharpened common end to assist the needle in entering the skin and penetrating flesh necessary to reach the target region.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS

Broadly, the present invention concerns a method and apparatus for destroying a target region of tissue by saturating the region with light-absorbing material, reducing the temperature of the region, and disintegrating the region with a light source. This invention therefore contemplates various process steps for eliminating the tissue, as well as an apparatus useful in carrying out steps such as these.

Structure

Figure 1:
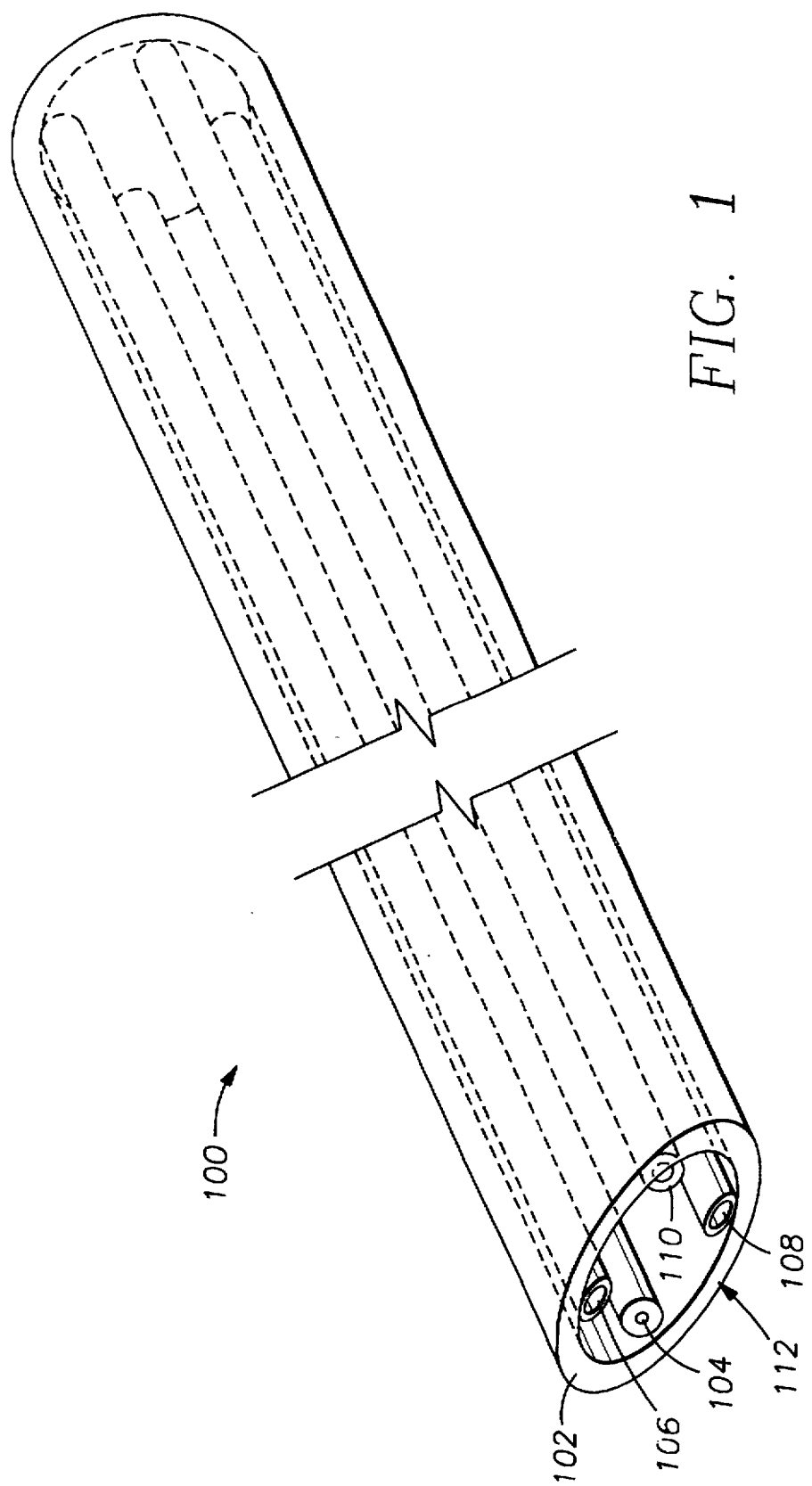
FIG. 1 is a perspective view of a multi-channel delivery needle of the invention.

In a preferred embodiment, the apparatus aspect of the invention comprises a multi-channel delivery needle 100, as shown in FIG. 1. The needle 100 includes a primary transport line 102 along with a number of accessories. The primary transport line 102 preferably comprises a 4 mm stainless steel or silver hollow tube of the type that biopsy needles are commonly made from.

The accessories include a waveguide 104, a coolant injector line 106, a stain injector line 108, and a visual guidance line 110. The waveguide 104 preferably comprises an optically transmissive medium such as a 0.5 mm plastic fiber optic cable, or another suitable component capable of propagating a laser light beam. For greater flexibility in operation, the waveguide 104 may comprise a 1–2 mm hollow stainless steel or silver sheath, housing a slidably removable optically transmissive medium. The coolant injector line 106 preferably comprises an optically transmissive medium such as a 1–2 mm stainless steel or silver tube of the type that hypodermic needles are commonly made from, or another component of material and construction suitable to transport cryogenic materials. The stain injector line 108 also preferably comprises a 1–2 mm stainless steel or silver tube of the type that hypodermic needles are commonly made from, or another adequate component of material and construction suitable to transport stains described herein. The guidance line 110 preferably comprises a 1–2 mm plastic or quartz fiber optic cable, or another suitable optical component of adequate material and construction to transport visual images from one of its ends to the other. To facilitate selective removal, the visual guidance line 110 may comprise a 1–2 mm hollow stainless steel or silver sheath housing the desired type of optically transmissive medium.

Each of the waveguide 104, coolant injector line 106, stain injector line 108, and visual guidance line 110 is preferably connected to the primary transport line 102 along a respective lengthwise seam, which may be soldered, heat bonded, glued, or attached by another suitable means. Preferably, each of the components 104, 106, 108, and 110 is mounted internal to the primary transport line 102, about the inner circumference of the line 102. These components together provide a common end 112 defining an edge or point with sufficient sharpness to puncture the intended type of bodily tissue. The sharpness of the end 112 may be created, for example, by filing, grinding, laser cutting, mechanically slicing, or other appropriate means.

During operation of the needle 100, the components of the needle 100 are preferably coupled to various sources, e.g. light, vacuum pressure, coolant, etc. For example, the waveguide 104 is preferably coupled to a laser light source, such as a Nd:YAG pulsed laser having a wavelength of 1.06 µm energy density of 5 J/cm$^2$, 0.5 mm spot size, 50 ns pulsewidth, and 10 Hz repetition rate. Although this laser is preferably Q-switched to produce short pulses in the nanosecond range, it may be operated in a free-running mode instead. It may also be frequency doubled to 0.532 µm, or frequency tripled to 0.355 µm. The Nd:YAG laser operating at 1.06 µm is advantageous in this application because it is poorly absorbed by un-stained bodily tissue, and therefore avoids or minimizes damage to neighboring healthy tissue. As an alternative, the laser source may comprise other frequency shifted wavelengths of Nd:YAG (e.g. 0.532 µm and 0.355 µm) as well as various solid state lasers, and other types of lasers such as indocyanine green, titanium, diode, dye, eximer, or another suitable type of laser.

The primary transport line 102 is preferably coupled to a vacuum source capable of selectively producing vacuum pressure, including a level of roughly 0.6–0.8×10$^5$ pascal/cm$^2$. Also, the coolant injector line 106 is preferably connected to a coolant source (not shown), including a cooled reservoir of cryogenic material and a pump to selectively direct controlled amounts of the coolant through the injector line 106. The cryogenic material may comprise, for example, liquid nitrogen, helium, air, or another cooled inert material.

The stain injector line 108 is preferably coupled to a stain source (not shown) including a stain reservoir and a pump to selectively direct a spray or stream of stain in a controlled volume through the injector 108. The stain may comprise a stain medically approved for internal use, such as India ink, that is also particular absorbent to the wavelength of the laser source. The visual guidance line 110 is preferably coupled, opposite the common end 112, to an endoscopic eyepiece or another suitable device for viewing images sampled at the common end 112.

Operation

In a preferred embodiment, the process aspect of the invention comprises a method for destroying a target region of tissue by saturating the region with light-absorbing material, reducing the temperature of the region, and disintegrating the region with a light source. The target region may comprise a region such as a tumor, fatty tissue, cyst, or the like. This system may be applied to humans as well as animals such as mammals, birds, reptiles, or other blooded animals.

Figure 2:
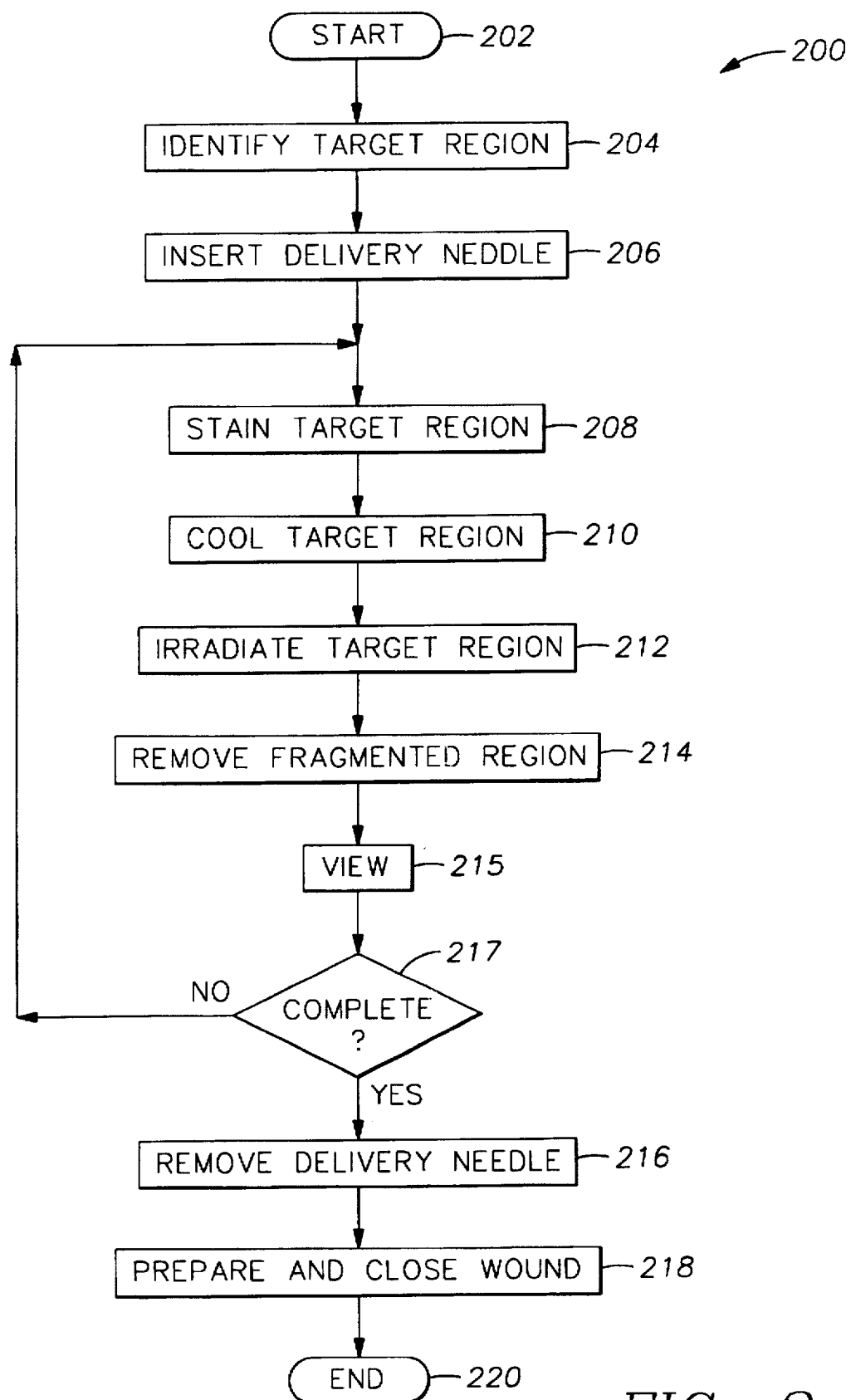
FIG. 2 is a flowchart depicting, an illustrative sequence of method steps in accordance with the invention.

The sequence 200 (FIG. 2) more particularly illustrates one embodiment of the process of the invention. For ease of discussion, the sequence 200 is described in the context of the multi-channel delivery needle 100, although skilled artisans with the benefit of this disclosure may implement the process of the invention with other hardware arrangements. First, in task 204 the target region (not shown) is identified. This may be performed using ultrasound exploration, x-ray exploration, tissue sampling, computer tomography ("CT"), magnetic resonance imaging ("MRI"), or other investigatory techniques.

Next, the delivery needle 100 is inserted into the patient's body (not shown) proximate the target region, in task 206. The common end 112 punctures the patient's skin, and penetrates the patient's flesh until it reaches the target region. Accurate guidance of the needle 100 to the target region may be aided by evaluating and re-directing the needle's path using images provided by the visual guidance line 110. After task 206, stain is directed to the target region in task 208 by pumping it through the stain injector line 108. Preferably, between 0.1 mL and 0.4 mL of stain is used, depending upon the size of the target region. To avoid obscuring the waveguide 104 and visual guidance line 110 during the staining of task 208, their optical components may be temporarily withdrawn as discussed above.

After task 208, the cryogenic material is transported through the coolant line 106 to cool the target region. Preferably, between 0.5 mL and 2 mL of coolant is used, depending upon the size of the target region. If liquid nitrogen is used, as in the illustrated embodiment, the coolant temperature is approximately 77° K. Preferably, the coolant is permitted to contact the target region for a sufficient time that the target region reaches the coolant's temperature. However, satisfactory results may be achieved in some cases by merely cooling the target region until it freezes. Nonetheless, the cooling of task 210 effectively creates a localized "stone" of hardened unwanted material which is stained with the laser-absorbent stain. If desired, any excess coolant may be withdrawn by reversing fluid pressure in the coolant line 106.

After the target region is sufficiently cooled, the laser light source directs its beam in task 212 through the waveguide 104, which directs the beam upon the cooled, stained target region. As an example, about 5 pulses of the laser beam may be administered in task 212. Due to the enhanced light-absorbency of the stained tissue, the laser irradiation creates a shock wave that fragments the "stone" of unwanted tissue.

If the target region is particularly large or resistant to fragmentation, the target region may be repeatedly stained, frozen, and irradiated, as necessary.

After task 212, the fragments are removed in task 214 by applying vacuum pressure to the primary transport line 102, thereby "sucking" the fragments up through the line 102.

Then, in task 215 the removed fragments are examined histologically to determine whether treatment is complete. Alternatively, in the case of non-malignant stone removal for example, the visual guidance line 110 may be used to view the target region to determine whether treatment is complete. If query 217 determines that treatment is not complete, the process is started again beginning at task 208. Otherwise, the process continues by removing the needle 100 in task 216, and preparing and closing the wound in task 218. In particular, task 218 may involve one or more injections of antibiotics, anti-cancer agents, blood coagulants, or other appropriate treatment. Also in task 218, the small wound caused by insertion of the needle 100 is closed by application of a bandage or, if necessary, placement of a sub-skin suture. Finally, the sequence 200 ends in task 220.

Other Embodiments

While there have been shown what are presently considered to be preferred embodiments of the invention, it will be apparent to those skilled in the art that various changes and modifications can be made herein without departing from the scope of the invention as defined by the appended claims.

For example, in an alternative embodiment the sequence 200 the target region may be cooled before staining, reversing steps 208 and 210.

In an alternative embodiment of the needle 100, a lesser number of accessory lines may be used, where one or more accessory lines are shared. For example, the coolant line 106 and stain injector line 108 may comprise a single, shared line. Moreover, the waveguide 104 and visual guidance line 110 may comprise a single shared line, used for the two respective purposes at different times. Alternatively, a single accessory line may be used to convey coolant, stain, and removable optical conduits at different times. As another alternative, the primary transport line 102 may be used, in addition to its tissue removal function, to deliver coolant, stain, or laser light to the target region instead of one or more of the accessory lines.

What is claimed is:

1. A method for treating tissue of a living body, comprising:
   increasing tendency of a target region of tissue internal to the living being to absorb a selected type of light by staining the target region with a selected color of stain;
   reducing temperature of the target region to a selected temperature no greater than zero degrees Celsius; and
   breaking the target region tissue into multiple pieces by irradiating the target region with the selected type of light.
2. The method of claim 1, further comprising removing pieces of target region tissue from the body.
3. The method of claim 1, wherein the irradiating is performed with a laser.
4. The method of claim 3, wherein the laser comprises a Nd:YAG laser.
5. The method of claim 1, wherein the reducing of the target region temperature is performed with a cryogenic liquid.
6. The method of claim 5, wherein the cryogenic liquid comprises liquified nitrogen.
7. The method of claim 1, wherein the target region of tissue comprises a tumor.
8. The method of claim 1, wherein the target region of tissue comprises fatty tissue.
9. The method of claim 1, wherein the selected temperature comprises zero degrees Celsius.
10. The method of claim 1, further comprising identifying the target region prior to staining the target region.
11. The method of claim 10, wherein the identifying is performed by ultrasound imaging.
12. The method of claim 10, wherein the identifying is performed by x-ray imaging.
13. The method of claim 1, wherein the staining of the target region is performed prior to the reducing of the temperature of the target region.
14. The method of claim 1, wherein the reducing of the temperature of the target region is performed prior to the staining of the target region.
15. The method of claim 1, wherein the stain comprises India ink.
16. The method of claim 1, wherein the selected type of light comprises light produced by a Q-switched laser.
17. A method for treating tissue from a living body, comprising:
   inserting a number of conveyance lines into a target of tissue in the living body;
   injecting a volume of stain through at least one of said conveyance lines into a target region of tissue internal to a living being, said stain selected to increase absorbency of the target region to a selected type of light;
   injecting a cryogenic substance into the target region through at least one of said conveyance lines to substantially freeze the target region; and
   breaking the target region tissue into multiple pieces by projecting light of the selected type to the target region through at least one of said conveyance lines.
18. The method of claim 17, further comprising applying a selected level of vacuum pressure to at least one of said at least one conveyance lines.
19. The method of claim 17, wherein the light is generated by a laser.
20. The method of claim 19, wherein the laser comprises a Nd:YAG laser.
21. The method of claim 17, wherein the cryogenic substance comprises a liquid.
22. The method of claim 21, wherein the cryogenic liquid comprises liquified nitrogen.
23. The method of claim 17, wherein the target region of tissue comprises a tumor.
24. The method of claim 17, wherein the target region of tissue comprises fatty tissue.
25. The method of claim 17, wherein the injecting of the cryogenic substance comprises injecting a cryogenic substance into the target region through at least one of said conveyance lines to reduce temperature of the target region to a selected temperature no greater than zero degrees Celsius.
26. The method of claim 17, wherein the target region of tissue includes non-solid tissue, and the injecting of the cryogenic substance reduces temperature of the non-solid tissue sufficiently for the non-solid tissue to substantially solidify.
27. The method of claim 17, wherein said conveyance lines include a hollow needle.
28. The method of claim 17, wherein said conveyance lines include a laser waveguide.
29. The method of claim 17, wherein said conveyance lines include a central tube connected along a lengthwise seam to at least one secondary tube of smaller diameter.
30. The method of claim 17, further comprising identifying the target region prior to inserting the conveyance lines into the target region of tissue.
31. The method of claim 30, wherein the identifying is performed by ultrasound imaging.
32. The method of claim 30, wherein the identifying is performed by x-ray imaging.
33. The method of claim 17, wherein the number of conveyance lines comprises one.
34. The method of claim 19, the laser comprising a Q-switched laser.
35. A method of treating tissue of a living body, comprising:

inserting a cryogenic laser irradiation tool into a living body with sufficient penetration to reach a target region of tissue internal to a living being, the tool comprising:
   a needle defining a point sufficiently sharp to puncture a selected type of tissue, said needle including:
      a centrally hollow primary needle;
      a light-transmitting medium connected lengthwise to the primary needle; and
      at least one centrally hollow sub-needle connected lengthwise to the primary needle;
conveying a selected color of stain to the target region tissue via at least one of the sub-needles to increase a tendency of the target region tissue to absorb a selected type of light;
conveying a cryogenic fluid in sufficient amount and temperature to the target region tissue via at least one of the sub-needles to reduce temperature of the target region tissue to a selected temperature not greater than zero degrees Celsius; and
directing the selected type of light to the target region tissue via the light-transmitting medium to divide the target region tissue into multiple pieces.

36. A method of treating tissue of a living body, comprising:
   inserting a multi-channel delivery needle into a living body with sufficient penetration to reach a target region of tissue internal to a living being, the needle comprising:
      a transport line;
      a waveguide connected to the transport line along a lengthwise seam;
      at least one injector line connected to the transport line along a lengthwise seam; and
      wherein the transport, waveguide, and injector lines define a sharpened common end;
   conveying a selected color of stain to the target region tissue via at least one of the injector lines to increase a tendency of the target region tissue to absorb a selected type of light;
   conveying a cryogenic fluid in sufficient amount and temperature to the target region tissue via at least one of the injector lines to substantially freeze the target region tissue; and
   breaking the target region tissue into multiple pieces by directing the selected type of light to the target region tissue via the waveguide.

37. The method of claim 36, further comprising removing pieces of the target region tissue from the body via the transport line.

38. The method of claim 37, the removing of target region tissue pieces being performed by applying vacuum pressure to the transport line.

39. The method of claim 36, the selected type of light being generated by a laser.

40. The method of claim 39, the laser comprising a Nd:YAG laser.

41. The method of claim 39, the laser comprising a Q-switched laser.

42. The method of claim 36, the cryogenic fluid comprising a cryogenic liquid.

43. The method of claim 42, the cryogenic liquid comprising liquified nitrogen.

44. The method of claim 36, the target region tissue comprising a tumor.

45. The method of claim 36, the target region tissue comprising fatty tissue.

46. The method of claim 36, the conveying of the cryogenic fluid reducing temperature of the target region tissue to a selected temperature no greater than zero degrees Celsius.

47. The method of claim 36, further comprising identifying the target region prior to inserting the multi-channel delivery needle.

48. The method of claim 47, the identifying being performed by ultrasound imaging.

49. The method of claim 47, the identifying being performed by x-ray imaging.

50. The method of claim 36, the stain being conveyed to the target region before conveying the cryogenic fluid to the target region.

51. The method of claim 36, the stain being conveyed to the target region after conveying the cryogenic fluid to the target region.

52. The method of claim 36, the stain comprising India ink.

53. The method of claim 36, the at least one injector line comprising multiple injector lines.

54. The method of claim 36, the waveguide and the at least one injector line being housed within the transport line.

55. The method of claim 36, the waveguide and the at least one injector line being secured to a surface internal to the transport line.

56. The method of claim 36, the transport line comprising a metallic material.

57. The method of claim 36, the waveguide including a sheath housing a slidably removable optically transmissive medium.

58. The method of claim 36, the waveguide comprising an optically transmissive medium.

59. The method of claim 36, the multi-channel delivery needle further including a visual guidance line connected to the primary transport line along a lengthwise seam, said visual guidance line having a viewing end and having an objective end proximate the common end, the method further comprising said visual guidance line gathering images proximate the objective end and transmitting said images to the viewing end.

* * * * *